United States Patent
Johnston et al.

(10) Patent No.: US 11,208,435 B2
(45) Date of Patent: Dec. 28, 2021

(54) VERTICILIDE ENANTIOMER AND METHODS OF INHIBITING CARDIAC RYANODINE RECEPTOR-MEDIATED INTRACELLULAR CALCIUM RELEASE

(71) Applicant: Vanderbilt University, Nashville, TN (US)

(72) Inventors: Jeffrey N. Johnston, Nashville, TN (US); Suzanne Batiste, Nashville, TN (US); Bjorn C. Knollmann, Bethesda, MD (US); Daniel J Blackwell, Nashville, TN (US); Nieves Gomez-Hurtado, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/626,073

(22) PCT Filed: Jun. 25, 2018

(86) PCT No.: PCT/US2018/039355
§ 371 (c)(1),
(2) Date: Dec. 23, 2019

(87) PCT Pub. No.: WO2018/237394
PCT Pub. Date: Dec. 27, 2018

(65) Prior Publication Data
US 2020/0262872 A1 Aug. 20, 2020

Related U.S. Application Data

(60) Provisional application No. 62/524,292, filed on Jun. 23, 2017.

(51) Int. Cl.
*C07K 11/02* (2006.01)
*C07K 11/00* (2006.01)
*A61P 9/06* (2006.01)
*A61P 9/00* (2006.01)
*A61P 9/10* (2006.01)
*A61P 25/28* (2006.01)
*A61K 38/00* (2006.01)

(52) U.S. Cl.
CPC ............ *C07K 11/02* (2013.01); *A61P 9/06* (2018.01)

(58) Field of Classification Search
CPC . C07K 11/02; C07K 11/00; A61P 9/06; A61P 9/00; A61P 9/10; A61P 25/28; A61K 38/00
See application file for complete search history.

(56) References Cited

U.S. PATENT DOCUMENTS

2007/0254849 A1 11/2007 Chen et al.

FOREIGN PATENT DOCUMENTS

EP 1561820 A1 8/2015

OTHER PUBLICATIONS

Popugaeva, E., "Dysregulation of neuronal calcium homeostasis in Alzheimer's disease—A therapeutic opportunity?." Biochemical and biophysical research communications 483.4 (2017): 998-1004.*
National Institute on Aging (Alzheimer's Disease Fact Sheet, 2014; http://www.nia.nih.gov/publication/alzheimers-disease-fact-sheet ).*
Suzanne M. Batiste et al: Rapid synthesis of cyclic oligomeric depsipeptides with positional, stereochemical, and macrocycle size distribution control, Proceedings of the National Academy of Sciences, vol. 113, No. 52, Dec. 14, 2016 (Dec. 14, 2016), pp. 14893-14897.

* cited by examiner

*Primary Examiner* — John M Mauro
(74) *Attorney, Agent, or Firm* — Stites & Harbison PLLC; Richard S. Myers, Jr.

(57) ABSTRACT

The non-natural enantiomer (ent-(+)-verticilide) and uses for treatment of RyR2-mediated spontaneous $Ca^{2+}$ leak, arrhythmia and memory loss.

14 Claims, 3 Drawing Sheets

VERTICILIDE ENANTIOMER AND METHODS OF INHIBITING CARDIAC RYANODINE RECEPTOR-MEDIATED INTRACELLULAR CALCIUM RELEASE

RELATED APPLICATIONS

This application claims priority from International Patent Application No. PCT/US2018/039355, filed Jun. 25, 2018, which claims priority from U.S. Provisional Application Ser. No. 62/524,292 filed Jun. 23, 2017, the entire disclosures of which are incorporated herein by this reference.

GOVERNMENT SUPPORT

This invention was made with support from NIH grant numbers T32 NS 007491-16 (BCK, DJB), GM 063557 (JNJ), R01HL092097 (RC), R01 HL138539 (RC), R01HL128044 (BCK), R01HL124935 (BCK), R01HL088635 (BCK). The government has rights to this invention.

SUMMARY OF THE INVENTION

An embodiment of the present invention is a novel, non-natural enantiomer of a depsipeptide natural product. It was discovered to be a potent and selective inhibitor of intracellular cardiac calcium release and antiarrhythmic agent.

$Ca^{2+}$ leak, or calcium release via ryanodine receptor type 2 (RyR2) can cause potentially fatal arrhythmias in a variety of heart diseases and has also been implicated in neurodegenerative and seizure disorders, making RyR2 an attractive therapeutic target for drug development. Here, the present inventors synthesized and investigated the fungal natural product and known insect RyR agonist (−)-verticilide, and several congeners to determine their activity against mammalian RyR2. Although the cyclooligomeric depsipeptide natural product (−)-verticilide had no effect relative to control, the newly discovered non-natural enantiomer (ent-(+)-verticilide) of the present invention significantly reduced RyR2-mediated spontaneous $Ca^{2+}$ leak both in wild-type cardiomyocytes and in cardiomyocytes from a gene-targeted mouse model of $Ca^{2+}$ leak-induced cardiac arrhythmias (Casq2$^{-/-}$). ent-(+)-Verticilide selectively inhibited type 2 RyR-mediated $Ca^{2+}$ leak and exhibited higher potency and a distinct mechanism of action compared to the non-selective RyR inhibitor tetracaine and the clinically-approved antiarrhythmic drug flecainide. ent-(+)-Verticilide attenuated ventricular arrhythmia in catecholamine-challenged Casq2$^{-/-}$ mice. These findings indicate that the compound of the present invention, ent-(+)-verticilide is a potent and selective inhibitor of RyR2-mediated diastolic $Ca^{2+}$ leak, making it a new molecular tool to target RyR2 mediated $Ca^{2+}$ leak in heart and brain pathologies. The compound of the present invention does not exist in nature and harbors unprecedented superior and unexpected activity.

One embodiment of the present invention is a non-natural enantiomer (mirror image) of a natural product ((−)-verticilide), prepared by chemical synthesis. This new chemical entity is referred to as ent-(+)-verticilide. It was found to inhibit ryanodine-mediated (RyR2) calcium flux, more potently than flecainide, for example, in cardiac myocytes. Furthermore, it exhibits a behavior that is unique in nature to flecainide and tetracaine.

Thus, an embodiment of the present invention is a compound of the following formula:

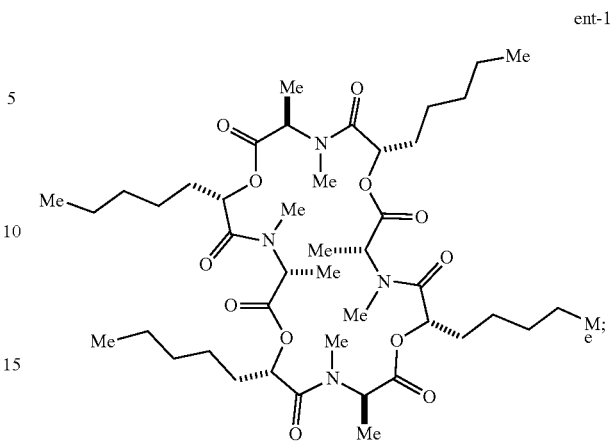

or a pharmaceutically acceptable salt thereof.

Another embodiment of the present invention is a pharmaceutical composition comprising a compound of the following formula:

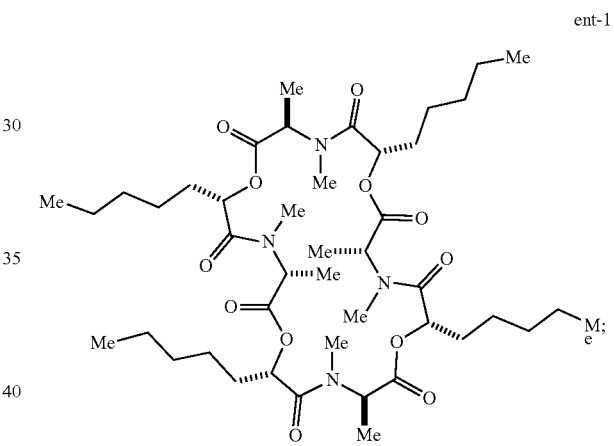

or a pharmaceutically acceptable salt thereof, and a pharmaceutically acceptable carrier.

Another embodiment of the present invention is a method for treating, preventing, or ameliorating at least one symptom associated with a heart disease or condition, comprising administering to a subject an effective amount of a compound or composition of the present invention. In embodiments of the present invention, the heart disease is heart failure, atrial fibrillation, arrhythmia, and CPVT.

Another embodiment of the present invention is a method of treating arrhythmia in a subject in need thereof, comprising the step of administering to the subject a compound or composition of the present invention in a dosage and amount effective to treat the arrhythmia.

Another embodiment of the present invention is a method of supressing $Ca^{2+}$ leak in a subject in need thereof, comprising the step of administering to the subject a compound or composition of the present invention in a dosage and amount effective to supress the $Ca^{2+}$ leak.

Another embodiment of the present invention is treating memory loss in a subject in need thereof, comprising the step of administering to the subject a compound or composition of the present invention in a dosage and amount effective to treat the memory loss.

Another embodiment of the present invention is inhibiting RyR2 in a subject in need thereof, comprising the step of administering to the subject a compound or composition of the present invention in a dosage and amount effective to inhibit RyR2.

Another embodiment of the present invention is a method of treating arrhythmia comprising the step of co-administering to the subject a compound or composition of the present invention in a dosage and amount effective to treat arrhythmia with a drug known to treat arrhythmia.

Another embodiment of the present invention is a method of treating Alzheimer's disease, comprising the step of co-administering to the subject a compound or composition of the present invention in a dosage and amount effective to treat arrhythmia with a drug known to treat Alzheimer's disease.

Other embodiments of the present invention include uses of a compound of the following formula:

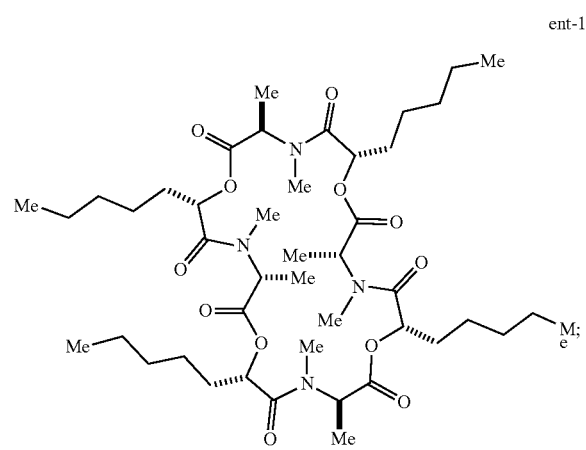

ent-1 or a pharmaceutically acceptable salt thereof, for the indications described herein.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

(FIG. 2A) Representative confocal line scans of Ca2+ sparks in the absence (DMSO) or presence of 25 μM nat-1 or ent-1 in permeabilized Casq2−/− cardiomyocytes. (FIG. 2B) Ca2+ spark frequency in Casq2−/− cells treated with 25 μM nat-1, 7, 8, and their respective enantiomers. (FIG. 2C) Comparison of [3H] ryanodine binding to SR isolated from porcine longissimus dorsi (RyR1) or cardiac ventricle (RyR2) in the presence of 50 μM nat-1, ent-1, or tetracaine (tet). (FIG. 2D) Dose response curves for ent-1 and tet inhibition of [3H]ryanodine binding to RyR2. (FIG. 2E) Representative Ca2+ sparks from permeabilized wild-type cardiomyocytes treated with 3 μM ent-1, 25 μM flecainide, or 50 μM tetracaine. Graph indicates amplitude of Ca2+ release of the selected representative sparks over time. (FIG. 2F) Percent change in spark frequency, amplitude, mass, leak, and SR Ca2+ content relative to vehicle (DMSO), obtained from wild-type myocytes. SR Ca2+ content was measured as the Ca2+ transient amplitude elicited by application of 10 mM caffeine (n≥5 cells per group). Data are presented as mean±SEM. N≥30 cells per group for A, B, and F. N=4 replicates for each concentration tested in C and D. *p<0.05 vs DMSO, p<0.01 vs DMSO, *p<0.001 vs DMSO by 1-way ANOVA with Tukey's post-hoc test (B) or t-test (C, D, and F).

(FIG. 3A) Isolated cardiomyocytes were field stimulated at 3 Hz for 20 seconds followed by 40 seconds recording of SCR events (†). Application of 10 mM caffeine (caff) was used to measure SR Ca2+ content. (FIG. 3B) SCR frequency following cessation of pacing. N=63, 27, 31, 63, 30, and 27 cells for 0, 0.03, 0.1, 0.3, and 1.0 μM ent-1, respectively. p<0.01, *p<0.001 vs DMSO by t-test. (FIG. 3C) Representative heart rate traces in Casq2−/− mice treated with DMSO or ent-1. Isoproterenol (3.0 mg/kg i.p.) was injected at 0 s. Rhythm strips show arrhythmia features. Ectopic beats (†) produce a variable HR in the traces. (FIG. 3D) Quantification of catecholamine-induced ectopic beats by surface electrocardiogram in Casq2−/− mice injected intraperitoneally with 30 mg/kg (drug/body weight) nat-1 or ent-1 or DMSO of equivalent volume 30 minutes prior to recordings. *p<0.001 vs DMSO or ###p<0.001 vs nat-1 by Mann-Whitney U-test. (FIG. 3E**) Incidence of ventricular tachycardia (VT). p=0.0305 for ent-1 vs DMSO (*) or ent-1 vs nat-1 (#) by Fisher's exact test. N=22 mice per group (D and E). Data in B and D presented as mean±SEM.

DESCRIPTION OF THE INVENTION

Figure 1:
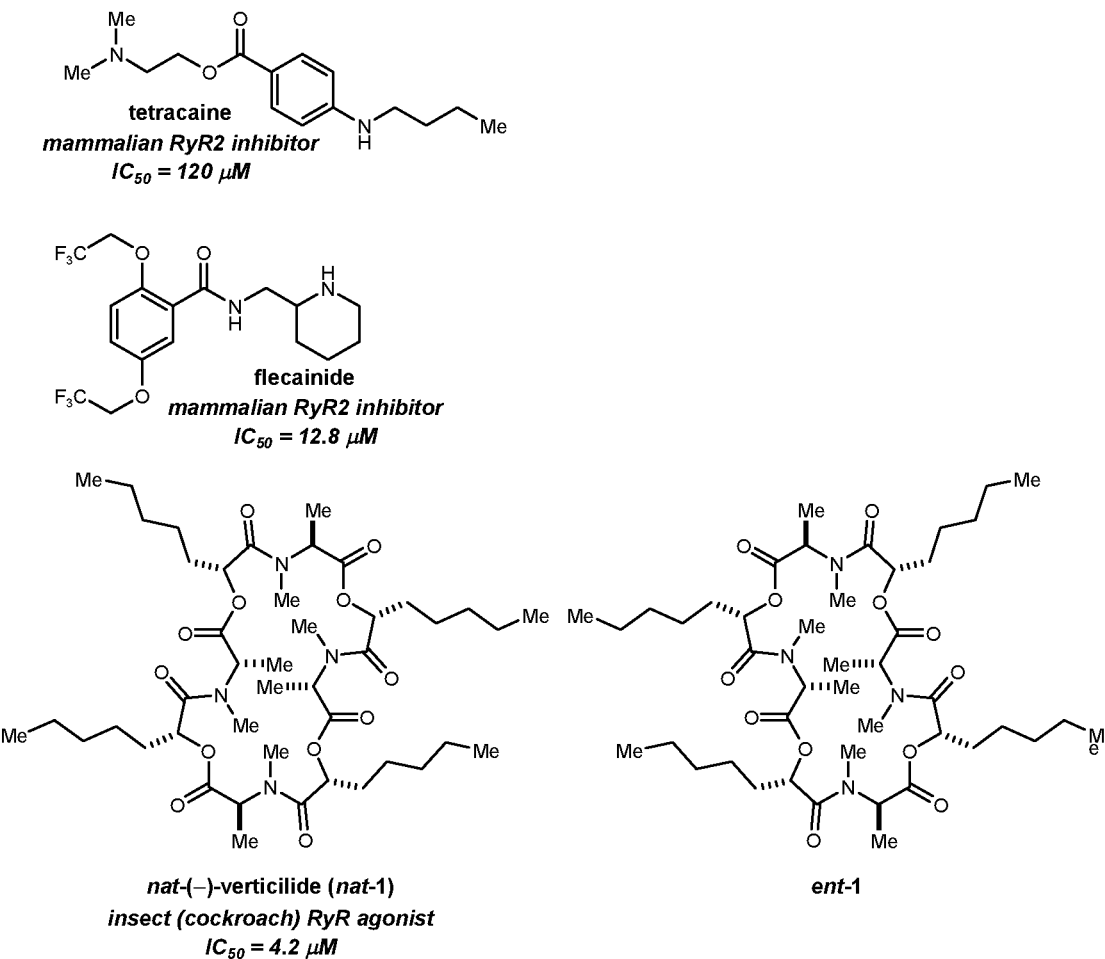
FIG. 1 shows compounds discussed in this specification.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise.

Ranges can be expressed herein as from "about" one particular value, and/or to "about" another particular value.

When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The compounds of the present invention are understood to include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

Thus, one aspect of the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compound (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The ryanodine receptor (RyR) is an intracellular $Ca^{2+}$ release channel that plays a critical role in excitable tissue. Mammals have three RyR isoforms: RyR1 and RyR2, which are abundantly expressed in skeletal and cardiac muscle, respectively, and RyR3, which has a broad expression profile, usually co-expressing with RyR1 or 2. Neuronal expression of RyR varies, but RyR2 is most abundant. In the brain, spontaneous $Ca^{2+}$ leak via RyR2 is implicated in a number of diseases, including Alzheimer's disease (AD), memory loss, neurodegeneration, and seizures. Increased neuronal RyR2 mRNA and protein expression have been found in patients with mild cognitive impairment and AD. Patients with AD have a variety of posttranslational modifications that increase RyR2-mediated $Ca^{2+}$ leak and accelerate the development of symptoms. Other neuropathies are associated with specific point mutations in RyR2 or its regulatory partners. Therapies aimed at stabilizing RyR2 and reducing $Ca^{2+}$ leak support the hypothesis that this protein complex is involved in a diverse range of neuropathies. Genetic ablation of the RyR2 PKA-mediated phosphorylation site reduced $Ca^{2+}$ leak and ameliorated AD symptoms and disease progression in an AD mouse model. The pan-RyR inhibitor, dantrolene, has been shown to be neuroprotective in mouse models of Huntington's disease, cerebral ischemia, and spinocerebellar ataxia type 2 and 3, suggesting a direct role for RyR2-mediated $Ca^{2+}$ leak.

In the heart, RyR2 mediates excitation-contraction (EC) coupling and opening of RyR2 channels is tightly regulated. Abnormally high RyR2 activity during diastole causes EC-coupling-independent spontaneous intracellular $Ca^{2+}$ release from the sarcoplasmic reticulum (SR) and has been documented in human heart diseases associated with both atrial and ventricular arrhythmia (i.e., heart failure, atrial fibrillation). Mutations in RyR2 and its binding partners that increase SR $Ca^{2+}$ leak cause primary atrial and ventricular arrhythmia syndromes such as catecholaminergic polymorphic ventricular tachycardia (CPVT), providing strong evidence for the mechanistic contribution of RyR2 to arrhythmia risk in humans. Further support comes from gene-targeted mouse models of CPVT, where catecholamine-induced spontaneous $Ca^{2+}$ release from the sarcoplasmic reticulum (SR) via RyR2 generates potentially fatal cardiac arrhythmias. Previously, the present inventors discovered that an antiarrhythmic small molecule drug currently in clinical use, flecainide (See FIG. 1), reduced CPVT episodes both in CPVT patients and in a calsequestrin knockout ($Casq2^{-/-}$) mouse model of CPVT. Although flecainide effectively suppresses RyR2-mediated spontaneous $Ca^{2+}$ release in CPVT cardiomyocytes, recent work suggests that the flecainide mode of action cannot be explained based on studies of single RyR2 channels incorporated in artificial lipid bilayers. Furthermore, flecainide is only 30% effective in suppressing spontaneous $Ca^{2+}$ waves at 10 µM concentration. New small molecule tool-compounds are needed to understand regulation of cellular $Ca^{2+}$ flux and its potential as a pharmacologic target for the prevention of cardiac arrhythmias triggered by untimely $Ca^{2+}$ release through RyR2 channels. The present invention helps meet this need.

(−)-Verticilide (nat-1) is a fungal cyclooligomeric depsipeptide (COD) natural product, derived from alternating α-hydroxy acid and α-amino acid monomers. Fungal CODs are structurally privileged natural products as demonstrated by their broad spectrum of biological activities, including antibiotic, insecticidal, and antitumor activities. Some CODs bind ions and serve as transporters across cell membranes—a feature which may contribute to their bioactivity. Additionally, they have a number of structural features, such as ring size, degree of N-methylation, α-amino acid and α-hydroxy acid sidechains and respective D- and L-stereochemistry which can modulate their bioactivity. However, biosynthetic structural diversification is limited as fungal COD-producing nonribosomal peptide synthetases (NRPSs) are only capable of incorporating a limited number of side chains. More significantly, fungal NRPSs selectively activate a specific enantiomer in the condensation domain from a racemic mixture to be coupled with the next in the sequence; therefore, stereochemical variation does not occur naturally. Unlike terpene or polyketide natural products which can be found in nature as the racemate or as the opposite enantiomer from another organism, the opposite enantiomer of fungal COD natural products can only be accessed by chemical synthesis. Unfortunately, traditional chemical synthesis of CODs remains a challenging, slow process in many cases. As a consequence, the biological relevance of ent-COD natural products and other derivatives is largely under explored. The present inventors discovered potent biological activity and therapeutic potential of an unnatural small molecule, ent-(+)-verticilide, that contrasts the inactivity of its mirror image, (−)-verticilide, a naturally occurring COD.

(−)-Verticilide (nat-1, FIG. 1) was first isolated in 2006 from a culture broth of *Verticillium* sp. FKI-1033 by Ōmura and coworkers while screening for potential insecticides. Its structure was determined to be a 24-membered COD consisting of alternating (+)-(R)-2-hydroxyheptanoic acid and N-methyl-L-alanine residues. nat-(−)-Verticilide was found to be an RyR agonist, selectively binding insect RyR with an $IC_{50}$ value of 4.2 μM. Because insects have only one RyR isoform, (−)-verticilide is a promising lead for developing new insecticides. (−)-Verticilide weakly binds mouse RyR1 with an $IC_{50}$ value of 53.9 μM, but its affinity to mammalian RyR2 or RyR3 is unknown. Given its known RyR binding abilities, The present inventors hypothesized that verticilide may also act on mammalian RyR2. Data in connection with the present invention compare the biological activity of nat-(−)-verticilide, its enantiomer (ent-(+)-verticilide), and both of their synthetic precursors on RyR2-mediated $Ca^{2+}$ release in single cardiomyocytes isolated from wild-type mice and a mouse model of human CPVT. These data show the superior and unexpected results of the present invention.

Two approaches to the synthesis of verticilide were leveraged in order to obtain verticilide congeners needed to investigate activity against RyR2. First, nat-(−)-verticilide was synthesized using a macrocyclooligomerization approach from tetradepsipeptide seco-acid 3 in an 8-step longest linear sequence. To obtain the linear precursor to verticilide, the synthesis was diverted from common tetradepsipeptide intermediate 2 to ultimately access 7 through a series of convergent deprotection and coupling steps (See scheme 1, below, which shows macrocyclooligomerization (MCO) and Modular Convergent Routes to Verticilide: (a) $BF_3 \cdot OEt_2$, PhSH, $CH_2Cl_2$, rt, 85%; (b) $H_2$, Pd/C, EtOH/$CH_2Cl_2$ (10:1), rt, 97%; (c) DIAD, $PPh_3$, benzene, rt, 93%; (d) $AlCl_3$, $CH_3NO_2$, 0° C.→rt, 97%; (e) $AlCl_3$, $CH_2Cl_2$, 0° C.→rt, 97%; (f) DIAD, $PPh_3$, benzene, rt, 80%; (g) NaH, MeI, DMF, 0° C., 78%).

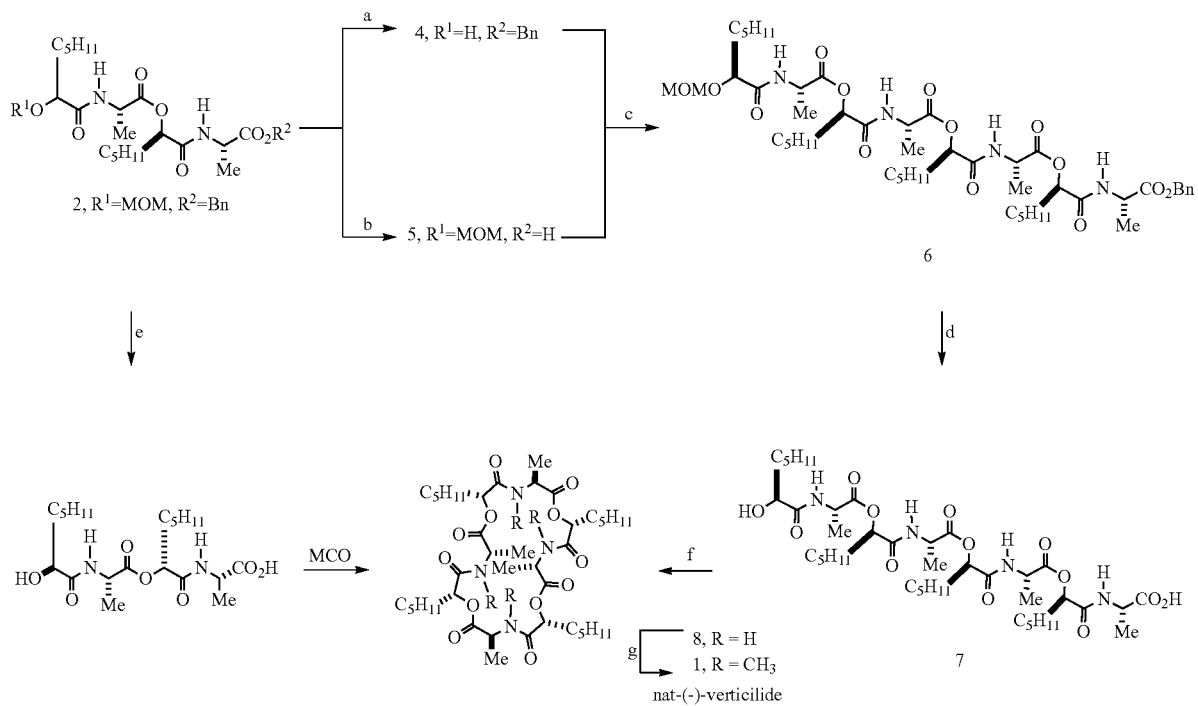

Scheme 1

Finally, 7 was subjected to Mitsunobu macrocyclization conditions to afford the 24-membered N—H precursor 8, which was transformed to nat-(−)-verticilide by per-N-methylation. Additionally, this simple, rapidly executed platform was used to prepare mirror image isomers ent-7, ent-8, and ent-(+)-verticilide (ent-1) in pure form (See Scheme 2, below, which shows the three step sequence to access enantiomeric depsipeptide building blocks.).

Scheme 1.

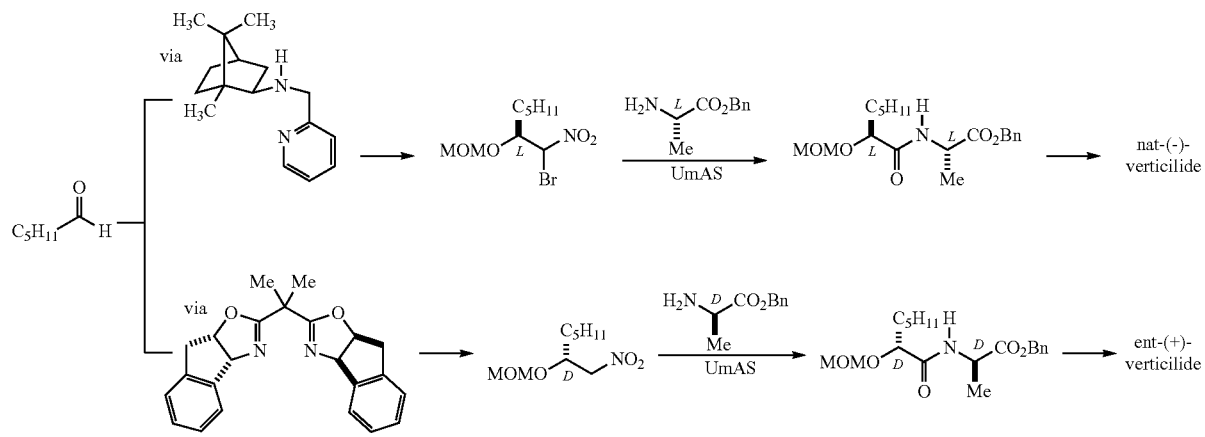

Figure 2:
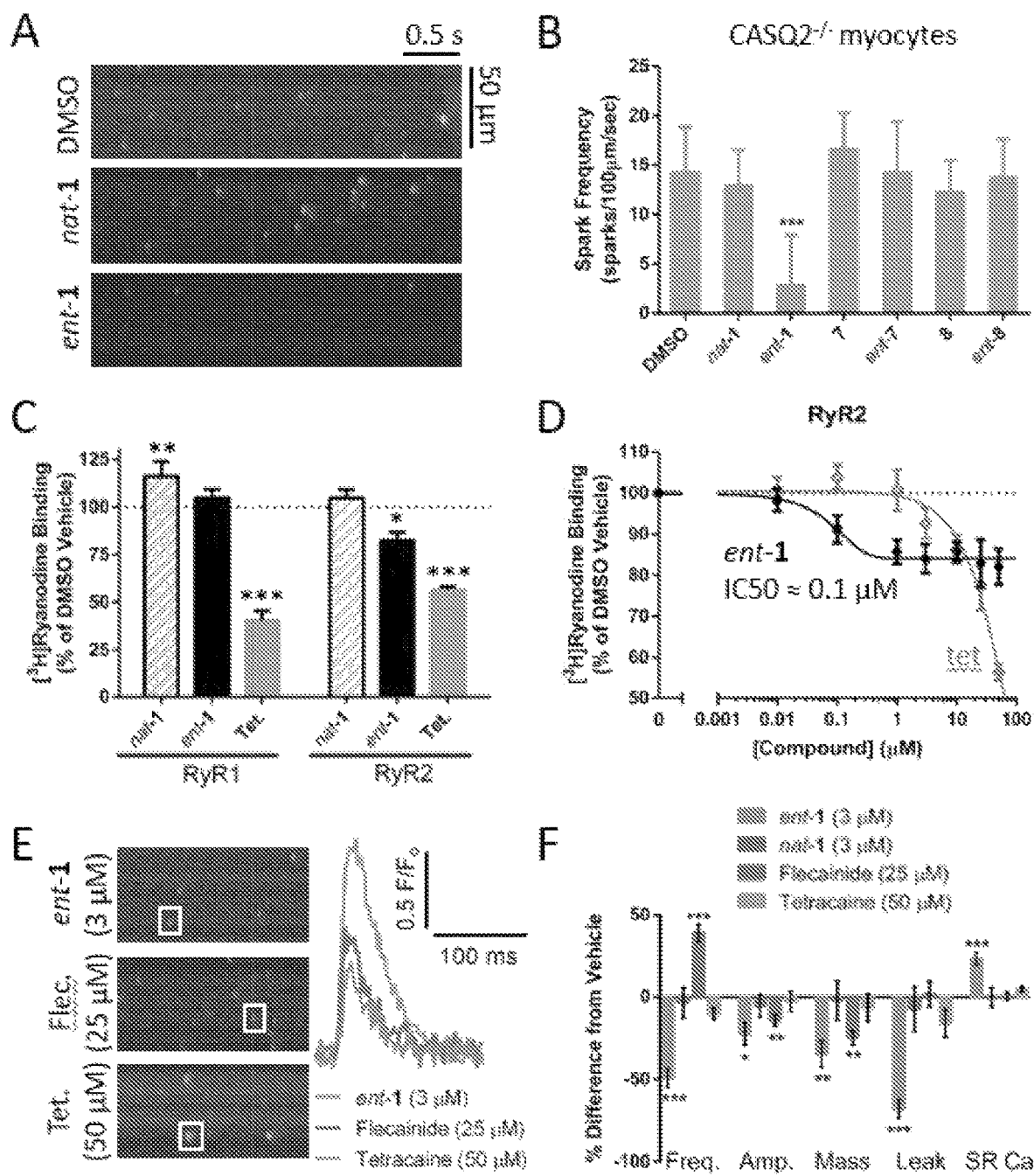
FIG. 2A-2F shows Ca2+ spark and [3H]ryanodine binding measurements of RyR activity.

The functional effects of natural-(−)- and unnatural ent-(+)-verticilide and their N—H congeners on RyR2 activity were investigated using Casq2 gene knockout (Casq2$^{-/-}$) mice, a validated model of human of CPVT that exhibits pathologically-increased RyR2 activity. Ventricular mouse myocytes were isolated, permeabilized with saponin to enable equivalent access of the compounds to the SR membrane, and incubated with DMSO or 25 µM nat- and ent-1, 7, 8. RyR2 activity was measured in the form of Ca$^{2+}$ sparks, which are elementary Ca$^{2+}$ release events generated by spontaneous openings of intracellular RyR2 Ca$^{2+}$ release channels. FIG. 2A shows representative confocal line scans for cells treated with DMSO, nat-1, or ent-1. Whereas nat-1 and the synthetic precursors had no effect on Ca$^{2+}$ sparks, ent-1 significantly reduced spark frequency (FIG. 2B), indicating that ent-1 inhibits RyR2-mediated Ca$^{2+}$ release. Cardiac SR Ca$^{2+}$ release is sensitive to the Ca$^{2+}$ concentration present at the cytosolic face of RyR2. To confirm that [Ca$^{2+}$]$_{free}$ was not altered by any of the compounds, Fluo-4 fluorescence was measured under spark assay conditions. The internal spark solution was incubated with DMSO or 25 µM nat-1, 7, 8, and their respective enantiomers for 10 minutes and [Ca$^{2+}$]$_{free}$ was calculated from a set of Ca$^{2+}$ standards.

To test whether ent-1 directly inhibits RyR, the present inventors measured [$^3$H]ryanodine binding—an index of RyR activity—to skeletal (RyR1) and cardiac (RyR2) porcine muscle SR preparations. Skeletal and cardiac SR were incubated with 50 µM nat-1, ent-1, and tetracaine for three hours. Nat-1 increased RyR1 activity, but had no effect on RyR2 (FIG. 2C). Conversely, ent-1 inhibited RyR2, but had no effect on RyR1. The well-established RyR inhibitor, tetracaine, inhibited both isoforms. Ent-1 was selected to generate full dose response curves for both cardiac and skeletal SR. Ent-1 inhibited RyR2 in a concentration-dependent manner with an apparent IC50 of approximately 0.1 µM and maximal inhibition of approximately 20% (FIG. 2D), but had no effect on RyR1 up to 50 µM (Figure S2). Ent-1 was a significantly more potent RyR2 inhibitor than the previously studied RyR inhibitors flecainide or tetracaine. To further characterize the Ca$^{2+}$ release inhibition by ent-1, the present inventors applied a lower concentration (3 µM) to wild type mouse myocytes and compared results to two other classical Ca$^{2+}$ release inhibitors, flecainide and tetracaine (representative line scans and sparks are shown in FIG. 2E). 3 µM ent-1 exhibited a dual effect on Ca$^{2+}$ sparks: a significant reduction in the rate of spontaneous Ca$^{2+}$ sparks (measured as spark frequency) and the amount of Ca$^{2+}$ released during each Ca$^{2+}$ spark (measured as spark amplitude and spark mass) (FIG. 2F). As a result, Ca$^{2+}$ spark mediated SR Ca$^{2+}$ leak was drastically reduced and was not a result of reduced SR Ca$^{2+}$ load (FIG. 2F). Interestingly, the effect of ent-1 on spark mass was analogous to flecainide, whereas the experimental RyR2 inhibitor tetracaine did not reduce spark mass. The effects of ent-1 on Ca$^{2+}$ spark frequency were similar to the RyR2 inhibitor tetracaine, but different from flecainide, which caused a paradoxical increase in spark frequency, in keeping with previous findings. Ent-1 significantly reduced Ca$^{2+}$ leak, whereas flecainide is a leak-neutral blocker. Taken together, our results demonstrate that ent-1 is not only a significantly more potent, but also a more effective Ca$^{2+}$ release inhibitor than flecainide and tetracaine and exhibits a different mechanism of action than other RyR inhibitors.

Nat-1 is capable of crossing cellular membranes based on its documented insecticidal activity and insect RyR inhibition. To test whether ent-1 crosses the sarcolemma, we measured spontaneous Ca$^{2+}$ release in intact Casq2$^{-/-}$ cardiomyocytes. Isolated cardiomyocytes were incubated for 3 hours with 0, 0.03, 0.1, 0.3, and 1.0 µM ent-1 and paced at 3 Hz for 20 seconds with 1.0 µM isoproterenol to stimulate adrenergic activation and a CPVT-like cellular phenotype consisting of spontaneous Ca$^{2+}$ release events (See FIG. 3A). Spontaneous Ca$^{2+}$ release can produce triggered beats that evoke ventricular ectopy and arrhythmogenesis. Ent-1 significantly reduced the frequency of spontaneous Ca$^{2+}$ release (FIG. 3B), suggesting that ent-1 is able to cross the sarcolemma and exerts biological activity. Inhibition of spontaneous Ca$^{2+}$ release mirrored the potency and dose dependence observed in the [$^3$H]ryanodine binding assay, but with a greater biological efficacy. Consistent with inhibition of RyR2-mediated Ca$^{2+}$ release, ent-1 reduced diastolic Ca$^{2+}$ levels, decreased Ca$^{2+}$ transient amplitude, and delayed time to peak of paced transients. Ent-1 did not alter SR Ca$^{2+}$ content or Ca$^{2+}$ decay kinetics, indicating that reduced SR load or impaired Ca$^{2+}$ reuptake do not account for the reduction in spontaneous Ca$^{2+}$ release.

Figure 3:
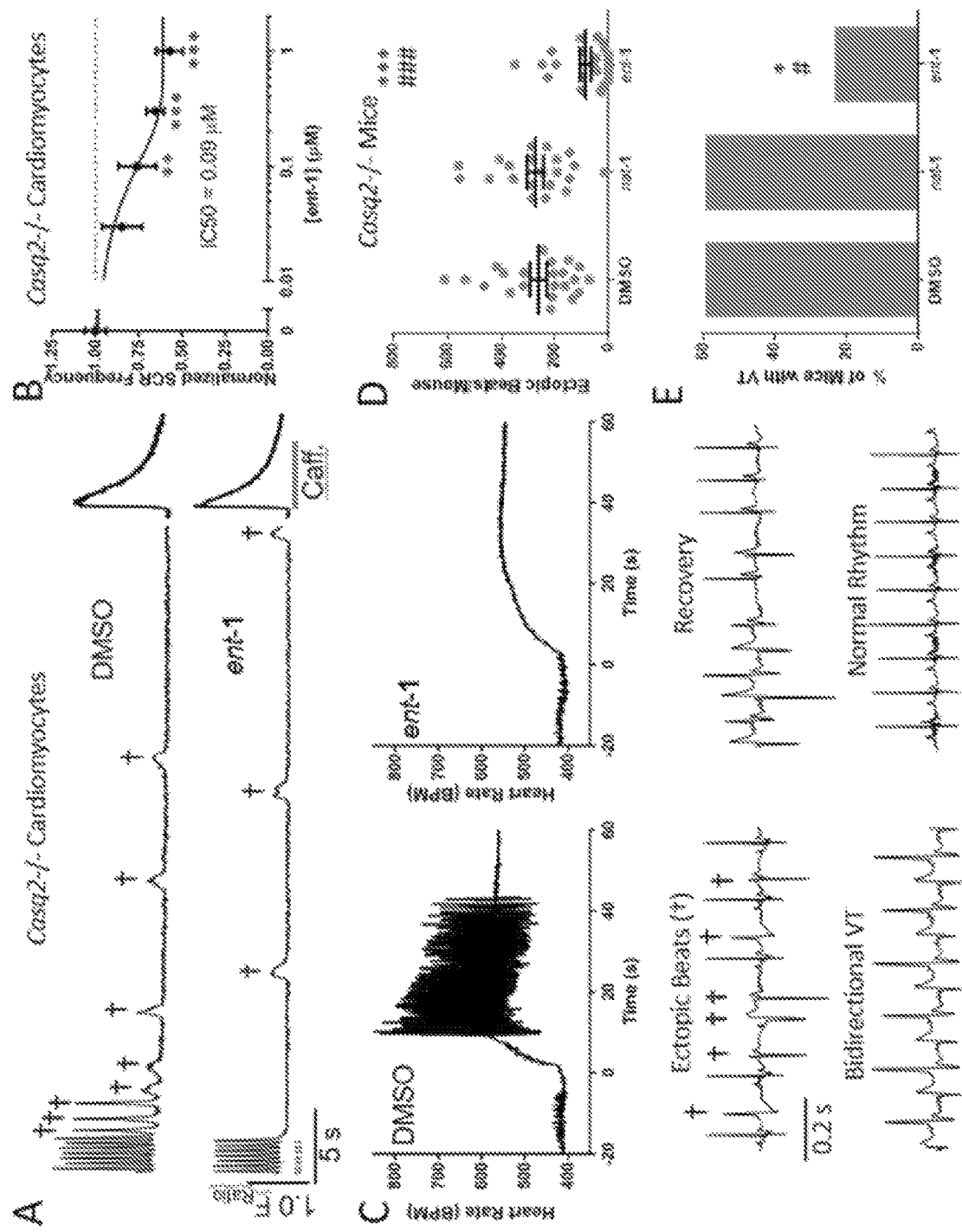
FIG. 3A-3E shows Ent-1 inhibition of spontaneous Ca2+ release (SCR) in isolated intact Casq2−/− cardiomyocytes and ventricular arrhythmia in mice.

To determine whether ent-1 inhibition of Ca$^{2+}$ release in cardiomyocytes in vitro translates into activity against ventricular arrhythmia in vivo, Casq2$^{-/-}$ mice were injected intraperitoneally with 30 mg/kg nat-1, ent-1, or DMSO of equivalent volume. After 30 minutes, mice were anesthetized with inhaled isoflurane and electrocardiogram recordings were made during intraperitoneal injection of 3.0 mg/kg isoproterenol to induce CPVT. FIG. 3C (first panel) illustrates the HR response to isoproterenol (0 s) and subsequent development of ventricular arrhythmias. Ent-1 significantly reduced the number of ventricular ectopic beats (FIG. 3C, D), primarily in the form of premature ventricular complexes. Ent-1 also reduced the incidence of ventricular tachycardia (FIG. 3E), an established risk factor for sudden cardiac death. There were no differences in baseline heart rate (HR) prior to isoproterenol; however, there was a significant reduction in peak HR and, consequently, ΔHR after isoproterenol injection in the ent-1 group. The HR reduction by ent-1 is consistent with its block of RyR2 channels in the sinoatrial node and hence the intracellular $Ca^{2+}$ clock responsible for HR acceleration in response to catecholamines. To exclude the possibility that the reduction in peak HR was responsible for the arrhythmia reduction by ent-1, we used a linear regression model to assess whether lower peak HR or ΔHR confer protection from ectopic beats. No association was found between peak or ΔHR and the number of ectopic beats in the DMSO and nat-1 groups. Hence, RyR2 inhibition by ent-1, rather than reduced peak HR or ΔHR, is responsible for the reduction in ectopic beats evinced by ent-1. Drugs that block cell membrane $Na^+$ or L-type $Ca^{2+}$ channels can prevent CPVT in mouse models and humans. To assess whether ent-1 in vivo efficacy was a result of $Na^+$ channel or $Ca^{2+}$ channel block, we measured the ECG QRS duration (prolonged by $Na^+$ channel blockers) and the PR interval (prolonged by $Ca^{2+}$ channel blockers). Ent-1 had no significant effect on QRS or PR interval, indicating that Na+ or $Ca^{2+}$ channel block by ent-1 does not contribute to its antiarrhythmic activity in vivo.

In the heart, RyR2-mediated $Ca^{2+}$ release plays a critical role in linking electrical excitation to mechanical contraction, a process known as EC coupling. Inappropriately timed $Ca^{2+}$ release can trigger arrhythmogenic events such as atrial or ventricular tachycardia and sudden death. Current therapeutic interventions with flecainide are capable of at least partially inhibiting $Ca^{2+}$ release mediated arrhythmias; however, new small-molecule tools are needed to further understand the role of $Ca^{2+}$ flux regulators and their relevance for preventing arrhythmias, especially since flecainide is contraindicated in patients with structural heart disease and heart failure. In the brain, inhibition of RyR2-mediated $Ca^{2+}$ leak has proven beneficial in preventing or delaying the onset of neuropathological symptoms in a variety of diseases. Our current investigation led us to examine the effects of a known insect RyR modulator, nat-(−)-verticilide, two synthetic precursors, and their mirror image isomers (ent). Whereas natural verticilide had no effect on mammalian RyR2, remarkably, we found that its enantiomer significantly inhibited RyR2-mediated $Ca^{2+}$ leak by a distinct mechanism of action compared to other RyR2 inhibitors.

ent-(+)-Verticilide significantly attenuated spontaneous $Ca^{2+}$ release in myocytes isolated from both a CPVT mouse model and wild-type mice. Importantly, nat-1, 7, 8, and their respective enantiomers did not bind to $Ca^{2+}$. The combined reduction of $Ca^{2+}$ spark frequency, amplitude, and mass resulted in a drastic reduction of $Ca^{2+}$ leak in the presence of ent-(+)-verticilide, which is a different mode of action than the prototype compounds tetracaine and flecainide. Tetracaine depresses spark frequency, but has no effect on $Ca^{2+}$ spark mass and only modestly reduces $Ca^{2+}$ leak. Flecainide reduces the amount of $Ca^{2+}$ released during a spark but increases spark frequency and hence has no net effect on $Ca^{2+}$ leak. These findings support different modes of action for these two compounds. Importantly, the dual and potent reduction of both spark frequency and spark mass suggests that ent-(+)-verticilide may be a prototype of a new class of RyR2 modulator that would be predicted to have superior activity against spontaneous $Ca^{2+}$ release compared to existing drugs such as flecainide. The effect on the $Casq2^{-/-}$ cardiomyocytes shows that ent-(+)-verticilide is effective for suppressing $Ca^{2+}$ leak, which has utility as a therapeutic intervention in heart diseases such as heart failure, atrial fibrillation, and CPVT, and neurological diseases such as Alzheimer's disease, seizures, and neurodegenerative disorders.

To probe the relationship between molecular structure and $Ca^{2+}$ spark suppression, we tested the effects of each enantiomer of verticilide and its linear and desmethyl cyclic precursors. Interestingly, ent-(+)-verticilide significantly decreased spontaneous $Ca^{2+}$ leak, but nat-(−)-verticilide did not have any effect. These results suggest that there is a specific ligand-receptor interaction between ent-(+)-verticilide and a chiral binding site in the cell. Enantiomer-dependent inhibition of RyR2-mediated $Ca^{2+}$ release has also been reported for the drug propafenone, which has antiarrhythmic properties similar to flecainide and is clinically used in racemic form. Compared to S-propafenone, R-propafenone is a significantly more potent inhibitor of RyR2 single channels in artificial bilayers and $Ca^{2+}$ sparks in cardiomyocytes. Similar to nat-(−)-verticilide, the linear congeners and their enantiomers did not exhibit an inhibitory effect. Hence, the cyclic form of ent-(+)-verticilide is also essential for activity. The amino acid sequence of insect RyR only shares about 45% homology with the mammalian isoforms. The carboxy-terminal portion of insect RyR, which forms the pore region of the $Ca^{2+}$ release channel, is highly conserved with over 90% homology with the corresponding region of the mammalian isoforms. However, insect and mammalian RyR isoforms differ greatly in the large amino-terminal portion of the channel, which extends into the cytosol and contains multiple binding sites for $Ca^{2+}$ release channel modulators. These regions of high divergence are possible candidates for ent-(+)-verticilide interaction with mammalian RyR2. It is unknown whether ent-(+)-verticilide binds to insect RyR, however the lack of effect of nat-(−)-verticilide on mammalian RyR2 is reassuring for developing it and its congeners as insecticides.

The data in the present specification show that the compound of the present invention is a potent inhibitor of intracellular $Ca^{2+}$ leak. Without being bound by theory of mechanism, the observed decrease in spontaneous $Ca^{2+}$ release by ent-(+)-verticilide may be due to direct binding to RyR2, or it may indirectly regulate RyR2 opening via accessory proteins. Previous studies have shown that calmodulin (CaM), $Ca^{2+}$-CaM Kinase II, and FK 506 proteins, among others, are all important regulators of RyR2 function. It is possible that ent-(+)-verticilide suppresses $Ca^{2+}$ leak by indirectly inhibiting RyR2 via one of these mechanisms. The present invention highlights a rare and exciting discovery of a novel compound that suppresses RyR2-mediated $Ca^{2+}$ leak, while a previously known corresponding natural product is completely inactive.

REFERENCES

Throughout this application, various publications are referenced. All such publications, including the ones listed below, are incorporated herein by reference in their entirety.

Yuan, Q., Deng, K. Y., Sun, L., Chi, S., Yang, Z., Wang, J., Xin, H. B., Wang, X. & Ji, G. Calstabin 2: An important regulator for learning and memory in mice. Sci. Rep. 6, 21087, (2016).

Johnson, J. N., Tester, D. J., Bass, N. E. & Ackerman, M. J. Cardiac channel molecular autopsy for sudden unexpected death in epilepsy. J. Child Neurol. 25, 916-921, (2010).

Lehnart, S. E., Mongillo, M., Bellinger, A., Lindegger, N., Chen, B. X., Hsueh, W., Reiken, S., Wronska, A., Drew, L. J., Ward, C. W., Lederer, W. J., Kass, R. S., Morley, G. & Marks, A. R. Leaky Ca2+ release channel/ryanodine receptor 2 causes seizures and sudden cardiac death in mice. J. Clin. Invest. 118, 2230-2245, (2008).

Bruno, A. M., Huang, J. Y., Bennett, D. A., Marr, R. A., Hastings, M. L. & Stutzmann, G. E. Altered ryanodine receptor expression in mild cognitive impairment and Alzheimer's disease. Neurobiol. Aging 33, 1001 e1001-1006, (2012).

Kelliher, M., Fastbom, J., Cowburn, R. F., Bonkale, W., Ohm, T. G., Ravid, R., Sorrentino, V. & O'Neill, C. Alterations in the ryanodine receptor calcium release channel correlate with Alzheimer's disease neurofibrillary and beta-amyloid pathologies. Neuroscience 92, 499-513, (1999).

Lacampagne, A., Liu, X., Reiken, S., Bussiere, R., Meli, A. C., Lauritzen, I., Teich, A. F., Zalk, R., Saint, N., Arancio, O., Bauer, C., Duprat, F., Briggs, C. A., Chakroborty, S., Stutzmann, G. E., Shelanski, M. L., Checler, F., Chami, M. & Marks, A. R. Post-translational remodeling of ryanodine receptor induces calcium leak leading to Alzheimer's disease-like pathologies and cognitive deficits. Acta Neuropathol. 134, 749-767, (2017).

Chen, X., Wu, J., Lvovskaya, S., Herndon, E., Supnet, C. & Bezprozvanny, I. Dantrolene is neuroprotective in Huntington's disease transgenic mouse model. Mol. Neurodegener. 6, 81, (2011).

Wei, H. & Perry, D. C. Dantrolene Is Cytoprotective in Two Models of Neuronal Cell Death. J. Neurochem. 67, 2390-2398, (2002).

Liu, J., Tang, T. S., Tu, H., Nelson, O., Herndon, E., Huynh, D. P., Pulst, S. M. & Bezprozvanny, I. Deranged calcium signaling and neurodegeneration in spinocerebellar ataxia type 2. J. Neurosci. 29, 9148-9162, (2009).

Chen, X., Tang, T. S., Tu, H., Nelson, O., Pook, M., Hammer, R., Nukina, N. & Bezprozvanny, I. Deranged calcium signaling and neurodegeneration in spinocerebellar ataxia type 3. J. Neurosci. 28, 12713-12724, (2008).

Bers, D. M. Cardiac excitation-contraction coupling. Nature 415, 198-205, (2002).

Wehrens, X. H. & Marks, A. R. Novel therapeutic approaches for heart failure by normalizing calcium cycling. Nat. Rev. Drug Discov. 3, 565-573, (2004).

Marks, A. R. Calcium cycling proteins and heart failure: mechanisms and therapeutics. J. Clin. Invest. 123, 46-52, (2013).

Dobrev, D., Carlsson, L. & Nattel, S. Novel molecular targets for atrial fibrillation therapy. Nat. Rev. Drug Discov. 11, 275-291, (2012).

Nattel, S., Burstein, B. & Dobrev, D. Atrial remodeling and atrial fibrillation: mechanisms and implications. Circ. Arrhythm. Electrophysiol. 1, 62-73, (2008).

Knollmann, B. C., Chopra, N., Hlaing, T., Akin, B., Yang, T., Ettensohn, K., Knollmann, B. E., Horton, K. D., Weissman, N. J., Holinstat, I., Zhang, W., Roden, D. M., Jones, L. R., Franzini-Armstrong, C. & Pfeifer, K. Casq2 deletion causes sarcoplasmic reticulum volume increase, premature Ca2+ release, and catecholaminergic polymorphic ventricular tachycardia. J. Clin. Invest. 116, 2510-2520, (2006).

Loaiza, R., Benkusky, N. A., Powers, P. P., Hacker, T., Noujaim, S., Ackerman, M. J., Jalife, J. & Valdivia, H. H. Heterogeneity of ryanodine receptor dysfunction in a mouse model of catecholaminergic polymorphic ventricular tachycardia. Circ. Res. 112, 298-308, (2013).

Kannankeril, P. J., Mitchell, B. M., Goonasekera, S. A., Chelu, M. G., Zhang, W., Sood, S., Kearney, D. L., Danila, C. I., De Biasi, M., Wehrens, X. H., Pautler, R. G., Roden, D. M., Taffet, G. E., Dirksen, R. T., Anderson, M. E. & Hamilton, S. L. Mice with the R176Q cardiac ryanodine receptor mutation exhibit catecholamine-induced ventricular tachycardia and cardiomyopathy. Proc. Natl. Acad. Sci. U.S.A. 103, 12179-12184, (2006).

Watanabe, H., Chopra, N., Laver, D., Hwang, H. S., Davies, S. S., Roach, D. E., Duff, H. J., Roden, D. M., Wilde, A. A. & Knollmann, B. C. Flecainide prevents catecholaminergic polymorphic ventricular tachycardia in mice and humans. Nat. Med. 15, 380-383, (2009).

Galimberti, E. S. & Knollmann, B. C. Efficacy and potency of class I antiarrhythmic drugs for suppression of Ca2+ waves in permeabilized myocytes lacking calsequestrin. J. Mol. Cell. Cardiol. 51, 760-768, (2011).

Bannister, M. L., Thomas, N. L., Sikkel, M. B., Mukherjee, S., Maxwell, C., MacLeod, K. T., George, C. H. & Williams, A. J. The mechanism of flecainide action in CPVT does not involve a direct effect on RyR2. Circ. Res. 116, 1324-1335, (2015).

Newman, D. J. & Cragg, G. M. Natural Products as Sources of New Drugs from 1981 to 2014. J. Nat. Prod. 79, 629-661, (2016).

Finefield, J. M., Sherman, D. H., Kreitman, M. & Williams, R. M. Enantiomeric natural products: occurrence and biogenesis. Angew. Chem. Int. Ed. Engl. 51, 4802-4836, (2012).

Noguchi, T., Oishi, S., Honda, K., Kondoh, Y., Saito, T., Ohno, H., Osada, H. & Fujii, N. Screening of a virtual mirror-image library of natural products. Chem. Commun. 52, 7653-7656, (2016).

Felicio, M. R., Silva, O. N., Goncalves, S., Santos, N. C. & Franco, O. L. Peptides with Dual Antimicrobial and Anticancer Activities. Front. Chem. 5, 5, (2017).

Sussmuth, R., Muller, J., von Dohren, H. & Molnar, I. Fungal cyclooligomer depsipeptides: from classical biochemistry to combinatorial biosynthesis. Nat. Prod. Rep. 28, 99-124, (2011).

Heitz, F., Kaddari, F., Heitz, A., Raniriseheno, H. & Lazaro, R. Conformations, cation binding, and transmembrane ion transfer properties of a cyclooctapeptide built by an alternation of D and L residues. Int. J. Pept. Protein Res. 34, 387-393, (1989).

Pitchayawasin, S., Kuse, M., Koga, K., Isobe, M., Agata, N. & Ohta, M. Complexation of cyclic dodecadepsipeptide, cereulide with ammonium salts. Bioorg. Med. Chem. Lett. 13, 3507-3512, (2003).

Kimura, S. & Imanishi, Y. Complex formation with alkali and alkaline earth metal ions of cyclic octapeptides, cyclo(Phe-Pro)4, cyclo(Leu-Pro)4, and cyclo[Lys(Z)-Pro]4. Biopolymers 22, 2383-2395, (1983).

Grell, E. & Funck, T. Carbon-13 nuclear-magnetic-resonance and infrared-absorption spectroscopy of valinomycin and its alkali-ion complexes. Eur. J. Biochem. 34, 415-424, (1973).

Patel, D. J. Carbon framework of valinomycin and its metal ion complex in solution. Biochemistry 12, 496-501, (1973).

Ovchinnikov, Y. A. Second FEBS-Ferdinand Springer lecture: Membrane active complexones. Chemistry and biological function. FEBS Lett. 44, 1-21, (1974).

Gao, M., Cheng, K. & Yin, H. Targeting protein-protein interfaces using macrocyclic peptides. Biopolymers 104, 310-316, (2015).

Villar, E. A., Beglov, D., Chennamadhavuni, S., Porco, J. A., Jr., Kozakov, D., Vajda, S. & Whiny, A. How proteins bind macrocycles. Nat. Chem. Biol. 10, 723-731, (2014).

Feifel, S. C., Schmiederer, T., Hornbogen, T., Berg, H., Sussmuth, R. D. & Zocher, R. In vitro synthesis of new enniatins: probing the alpha-D-hydroxy carboxylic acid binding pocket of the multienzyme enniatin synthetase. ChemBioChem 8, 1767-1770, (2007).

Pieper, R., Haese, A., Schroder, W. & Zocher, R. Arrangement of catalytic sites in the multifunctional enzyme enniatin synthetase. Eur. J. Biochem. 230, 119-126, (1995).

Xu, Y., Zhan, J., Wijeratne, E. M., Burns, A. M., Gunatilaka, A. A. & Molnar, I. Cytotoxic and Antihaptotactic beauvericin analogues from precursor-directed biosynthesis with the insect pathogen Beauveria bassiana ATCC 7159. J. Nat. Prod. 70, 1467-1471, (2007).

Monma, S., Sunazuka, T., Nagai, K., Arai, T., Shiomi, K., Matsui, R. & Omura, S. Verticilide: elucidation of absolute configuration and total synthesis. Org. Lett. 8, 5601-5604, (2006).

Shiomi, K., Matsui, R., Kakei, A., Yamaguchi, Y., Masuma, R., Hatano, H., Arai, N., Isozaki, M., Tanaka, H., Kobayashi, S., Turberg, A. & Omura, S. Verticilide, a new ryanodine-binding inhibitor, produced by *Verticillium* sp. FKI-1033. J. Antibiot. 63, 77-82, (2010).

Batiste, S. M. & Johnston, J. N. Rapid synthesis of cyclic oligomeric depsipeptides with positional, stereochemical, and macrocycle size distribution control. Proc. Natl. Acad. Sci. U.S.A. 113, 14893-14897, (2016).

Cheng, H., Lederer, W. J. & Cannell, M. B. Calcium sparks: elementary events underlying excitation-contraction coupling in heart muscle. Science 262, 740-744, (1993).

Meissner, G. Ryanodine receptor/Ca2+ release channels and their regulation by endogenous effectors. Annu. Rev. Physiol. 56, 485-508, (1994).

Rebbeck, R. T., Nitu, F. R., Rohde, D., Most, P., Bers, D. M., Thomas, D. D. & Cornea, R. L. S100A1 Protein Does Not Compete with Calmodulin for Ryanodine Receptor Binding but Structurally Alters the Ryanodine Receptor. Calmodulin Complex. J. Biol. Chem. 291, 15896-15907, (2016).

Hilliard, F. A., Steele, D. S., Laver, D., Yang, Z., Le Marchand, S. J., Chopra, N., Piston, D. W., Huke, S. & Knollmann, B. C. Flecainide inhibits arrhythmogenic Ca2+ waves by open state block of ryanodine receptor Ca2+ release channels and reduction of Ca2+ spark mass. J. Mol. Cell. Cardiol. 48, 293-301, (2010).

Schlotthauer, K. & Bers, D. M. Sarcoplasmic reticulum Ca(2+) release causes myocyte depolarization. Underlying mechanism and threshold for triggered action potentials. Circ. Res. 87, 774-780, (2000).

Knollmann, B. C. & Roden, D. M. A genetic framework for improving arrhythmia therapy. Nature 451, 929-936, (2008).

Lakatta, E. G., Maltsev, V. A. & Vinogradova, T. M. A coupled SYSTEM of intracellular Ca2+ clocks and surface membrane voltage clocks controls the timekeeping mechanism of the heart's pacemaker. Circ. Res. 106, 659-673, (2010).

Katz, G., Khoury, A., Kurtzwald, E., Hochhauser, E., Porat, E., Shainberg, A., Seidman, J. G., Seidman, C. E., Lorber, A., Eldar, M. & Arad, M. Optimizing catecholaminergic polymorphic ventricular tachycardia therapy in calsequestrin-mutant mice. Heart Rhythm 7, 1676-1682, (2010).

Khoury, A., Marai, I., Suleiman, M., Blich, M., Lorber, A., Gepstein, L. & Boulos, M. Flecainide therapy suppresses exercise-induced ventricular arrhythmias in patients with CASQ2-associated catecholaminergic polymorphic ventricular tachycardia. Heart Rhythm 10, 1671-1675, (2013).

Echt, D. S., Liebson, P. R., Mitchell, L. B., Peters, R. W., Obias-Manno, D., Barker, A. H., Arensberg, D., Baker, A., Friedman, L., Greene, H. L. & et al. Mortality and morbidity in patients receiving encainide, flecainide, or placebo. The Cardiac Arrhythmia Suppression Trial. N. Engl. J. Med. 324, 781-788, (1991).

Hwang, H. S., Hasdemir, C., Laver, D., Mehra, D., Turhan, K., Faggioni, M., Yin, H. & Knollmann, B. C. Inhibition of cardiac Ca2+ release channels (RyR2) determines efficacy of class I antiarrhythmic drugs in catecholaminergic polymorphic ventricular tachycardia. Circ. Arrhythm. Electrophysiol. 4, 128-135, (2011).

Xu, X., Bhat, M. B., Nishi, M., Takeshima, H. & Ma, J. Molecular cloning of cDNA encoding a drosophila ryanodine receptor and functional studies of the carboxyl-terminal calcium release channel. Biophys. J. 78, 1270-1281, (2000).

Balshaw, D. M., Xu, L., Yamaguchi, N., Pasek, D. A. & Meissner, G. Calmodulin binding and inhibition of cardiac muscle calcium release channel (ryanodine receptor). J. Biol. Chem. 276, 20144-20153, (2001).

Wehrens, X. H., Lehnart, S. E., Reiken, S. R. & Marks, A. R. Ca2+/calmodulin-dependent protein kinase II phosphorylation regulates the cardiac ryanodine receptor. Circ. Res. 94, e61-70, (2004).

Chelu, M. G., Danila, C. I., Gilman, C. P. & Hamilton, S. L. Regulation of ryanodine receptors by FK506 binding proteins. Trends Cardiovasc. Med. 14, 227-234, (2004).

Van Petegem, F. Ryanodine receptors: structure and function. J. Biol. Chem. 287, 31624-31632, (2012).

Hung, D. T., Nerenberg, J. B. & Schreiber, S. L. Distinct binding and cellular properties of synthetic (+)- and (−)-discodermolides. Chem. Biol. 1, 67-71, (1994).

Siddiqi, S. M., Chen, X., Schneller, S. W., Ikeda, S., Snoeck, R., Andrei, G., Balzarini, J. & De Clercq, E. Antiviral Enantiomeric Preference for 5'-Noraristeromycin. J. Med. Chem. 37, 551-554, (1994).

Logan, M. M., Toma, T., Thomas-Tran, R. & Du Bois, J. Asymmetric synthesis of batrachotoxin: Enantiomeric toxins show functional divergence against Nav. Science 354, 865, (2016).

Wade, D., Boman, A., Wahlin, B., Drain, C. M., Andreu, D., Boman, H. G. & Merrifield, R. B. All-D amino acid-containing channel-forming antibiotic peptides. Proc. Natl. Acad. Sci. U.S.A. 87, 4761-4765, (1990).

Tichenor, M. S., Trzupek, J. D., Kastrinsky, D. B., Shiga, F., Hwang, I. & Boger, D. L. Asymmetric total synthesis of (+)- and ent-(−)-yatakemycin and duocarmycin SA: evaluation of yatakemycin key partial structures and its unnatural enantiomer. J. Am. Chem. Soc. 128, 15683-15696, (2006).

Iwasa, E., Hamashima, Y., Fujishiro, S., Higuchi, E., Ito, A., Yoshida, M. & Sodeoka, M. Total synthesis of (+)-chaetocin and its analogues: their histone methyltransferase G9a inhibitory activity. J. Am. Chem. Soc. 132, 4078-4079, (2010).

Sando, L., Henriques, S. T., Foley, F., Simonsen, S. M., Daly, N. L., Hall, K. N., Gustafson, K. R., Aguilar, M. I. & Craik, D. J. A Synthetic mirror image of kalata B1 reveals that cyclotide activity is independent of a protein receptor. ChemBioChem 12, 2456-2462, (2011).

Boger, D. L. & Johnson, D. S. CC-1065 and the duocarmycins: unraveling the keys to a new class of naturally derived DNA alkylating agents. Proc. Natl. Acad. Sci. U.S.A. 92, 3642-3649, (1995).

Boger, D. L. & Hong, J. Asymmetric total synthesis of ent-(−)-roseophilin: assignment of absolute configuration. J. Am. Chem. Soc. 123, 8515-8519, (2001).

Farmer, R. L. & Scheidt, K. A. A Concise Enantioselective Synthesis and Cytotoxic Evaluation of the Anticancer Rotenoid Deguelin Enabled by a Tandem Knoevenagel/Conjugate Addition/Decarboxylation Sequence. Chem. Sci. 4, 3304-3309, (2013).

Wassermann, A. M., Lounkine, E., Hoepfner, D., Le Goff, G., King, F. J., Studer, C., Peltier, J. M., Grippo, M. L., Prindle, V., Tao, J., Schuffenhauer, A., Wallace, I. M., Chen, S., Krastel, P., Cobos-Correa, A., Parker, C. N., Davies, J. W. & Glick, M. Dark chemical matter as a promising starting point for drug lead discovery. Nat. Chem. Biol. 11, 958-966, (2015).

We claim:

1. A compound of the following formula:

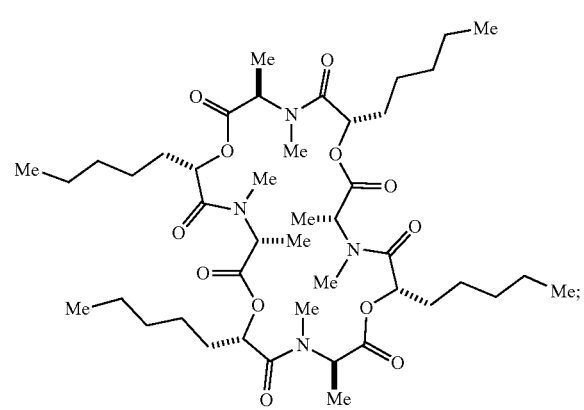

or a pharmaceutically acceptable salt thereof.

2. A pharmaceutical composition comprising a compound of claim 1 or a pharmaceutically acceptable salt thereof, and a pharmaceutically acceptable carrier.

3. A method for preventing, or ameliorating at least one of an atrial fibrillation, arrhythmia, or CPVT incident, comprising administering to a subject in need thereof an effective amount of a compound of the following formula:

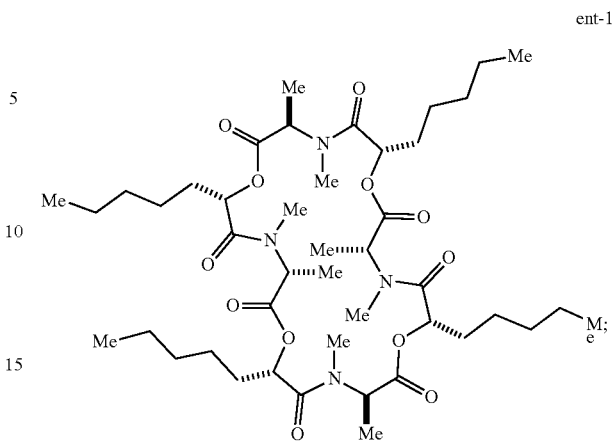

or a pharmaceutically acceptable salt thereof.

4. The method of claim 3, wherein said subject has been diagnosed with atrial fibrillation or arrhythmia.

5. The method of claim 3, wherein said subject is at risk of persistent atrial fibrillation or arrhythmia.

6. The method of claim 3, wherein said subject has had at least one prior incident of atrial fibrillation or arrhythmia.

7. The method of claim 6, wherein said administering step reduces the likelihood of future incidents of atrial fibrillation or arrhythmia in said subject.

8. The method of claim 6, wherein said administering reduces the likelihood of said atrial fibrillation or arrhythmia from becoming persistent or permanent.

9. The method of claim 3, wherein said subject is a human.

10. A method of improving symptoms of memory loss associated with Alzheimer's disease in a subject in need thereof, comprising administering to said subject an effective amount of a compound of the following formula:

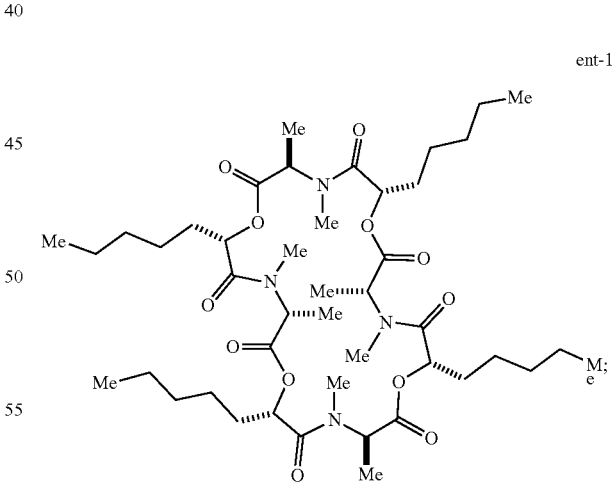

or a pharmaceutically acceptable salt thereof.

11. The method of claim 10, wherein said subject is a human.

12. The method of claim 10, wherein said subject has been diagnosed with Alzheimer's disease.

13. A method of improving symptoms of memory loss exacerbated by RyR2-mediated $Ca^{2+}$ leak in a subject in need thereof, comprising:

identifying a subject in need of stabilizing RyR2 and reducing $Ca^{2+}$ leak; and
administering to said subject an effective amount of a compound of the following formula:
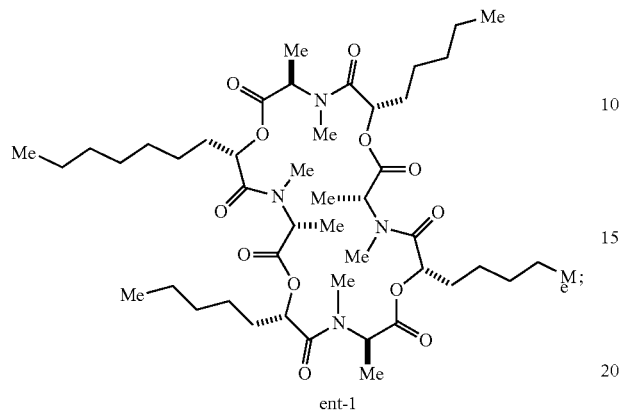
ent-1
or a pharmaceutically acceptable salt thereof.
14. The method of claim 13, wherein said subject has been diagnosed with memory loss.
* * * * *